[54] CERTAIN 3-PYRIDINIUMESTERS OF MONO- OR DI-LOWER ALKYL CARBAMATES HAVING ANTICHOLINESTERASE ACTIVITY

[75] Inventors: Nicholas S. Bodor, Gainesville, Fla.; Yasuo Ohshiro, Tokushima, Japan

[73] Assignee: Otsuka Pharmaceutical Co. Ltd., Tokyo, Japan

[21] Appl. No.: 578,958

[22] Filed: Feb. 10, 1984

[30] Foreign Application Priority Data

Feb. 10, 1983 [JP] Japan .................................. 58-21201

[51] Int. Cl.[4] .................... C07D 213/65; A61K 31/44
[52] U.S. Cl. ..................................... 514/346; 544/124; 544/360; 546/193; 546/281; 546/292
[58] Field of Search ........................ 546/292; 424/263; 514/346

[56] References Cited
U.S. PATENT DOCUMENTS 2,839,536   7/1958   Schnider et al. ..................... 546/292

FOREIGN PATENT DOCUMENTS

B1024505   2/1958   Fed. Rep. of Germany ...... 546/292

*Primary Examiner*—Alan L. Rotman
*Attorney, Agent, or Firm*—Burns, Doane, Swecker & Mathis

[57] ABSTRACT

Anticholinesterase and antihypercholesterolemic pyridine derivatives of the formula (I)

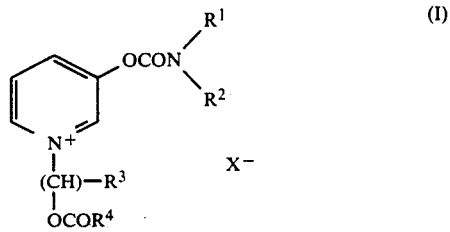

are provided as well as processes for preparing same, and composition and methods of treatment employing such pyridine derivatives as the active drug components thereof.

13 Claims, 1 Drawing Figure

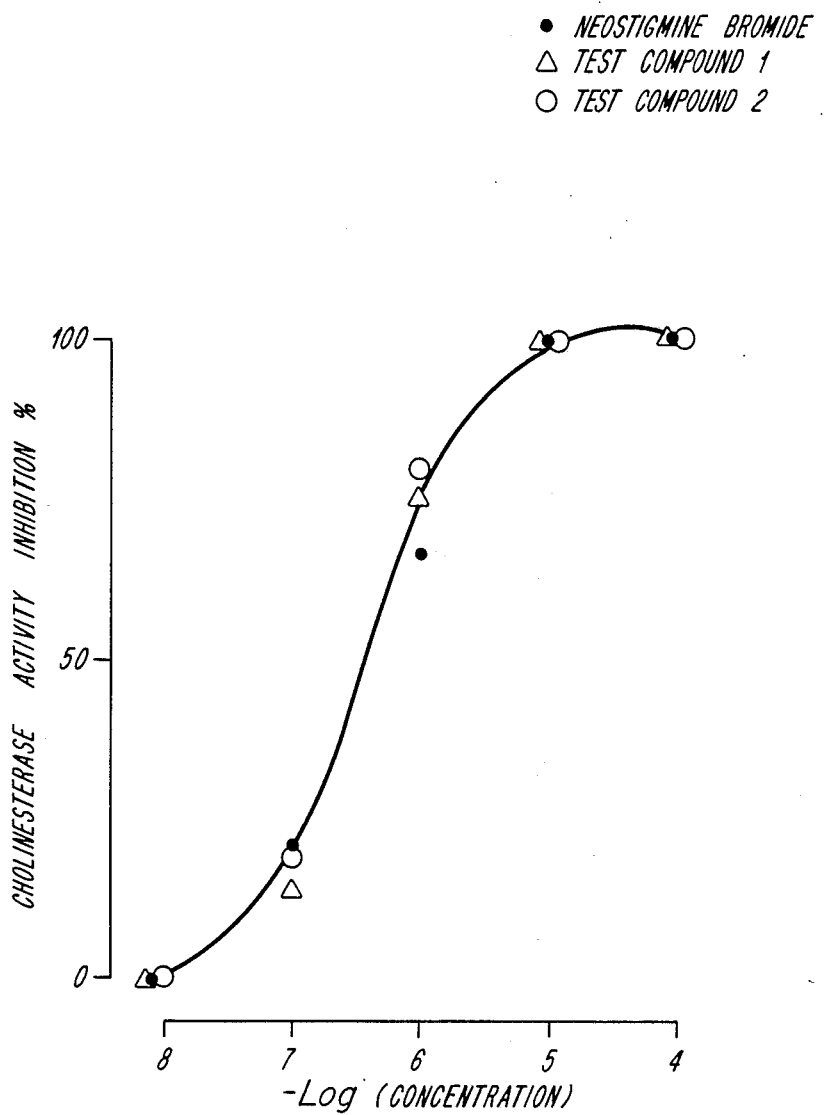

CERTAIN 3-PYRIDINIUMESTERS OF MONO- OR DI-LOWER ALKYL CARBAMATES HAVING ANTICHOLINESTERASE ACTIVITY

The present invention relates to novel pyridine derivatives, to processes for preparing the derivatives and to the use of same as effective cholinesterase inhibitors.

Compounds having cholinesterase inhibitory activity prevent the decomposition of acetylcholine in vivo and consequently exhibit the same activity as acetylcholine. Such anticholinesterase (anti-Che agents) cause acetylcholine to accumulate at cholinergic sites and thus are usable as pharmaceuticals in the treatment and management of the diseases against which acetylcholine is effective. Heretofore known compounds of this type however exhibit such toxicity levels that they are substantially unsuitable for practical therapeutic use.

As a component of their expanding biological profile, it has been found that cholinesterase inhibitors markedly reduce blood cholesterol and particularly low density lipoproteins (LDL) [K. M. Kutty, et al., Clin Biol. Chem., 8 379 (1975)]. Based on this finding, it has been strongly desired to develop a new class of drugs as potential blood cholesterol reducing agents with favorable cholineric activity and reduced toxicity.

Stemming from such research efforts to develop pharmaceuticals which are free from the high toxicity associated with conventional cholinesterase inhibitors but which retain the desired pharmacological activities, applicants have successfully prepared the novel pyridine derivatives of the present invention which possess very low toxicity while at the same time demonstrating excellent cholinesterase inhibitory activity.

The pyridine derivatives of the present invention comprise novel compounds of the formula (I) and nontoxic pharmaceutically acceptable salts thereof

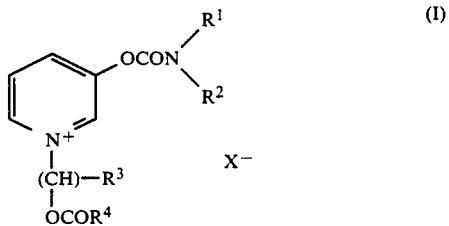

wherein $R^1$ and $R^2$ are the same or different and represent hydrogen, $C_1$-$C_8$ alkyl or together with the nitrogen atom to which they are attached form a 5 to 7 membered saturated or unsaturated heterocyclic ring containing 1 or 2 heteroatoms selected from O and N which may be the same or different and which ring may be optionally substituted by the group —$R^5$ representing $C_1$-$C_8$ alkyl, $C_6$-$C_{10}$ aryl, $C_1$-$C_8$ alkoxy, $C_1$-$C_8$ haloalkyl, $C_1$-$C_{20}$ alkoxy alkyl, $C_1$-$C_{20}$ alkanoyloxyalkyl, $C_3$14 $C_8$ cycloalkyl, $C_2$-$C_8$ alkenyl, or aryl substituted by $C_1$-$C_8$ alkyl, $C_1$-$C_8$ alkoxy, halogen, nitro, $C_1$-$C_8$ haloalkyl or $C_1$-$C_6$ acyloxy;

$R^3$ and $R^4$ are the same or different and represent hydrogen, $C_1$-$C_{20}$ alkyl, $C_6$-$C_{10}$ aryl, ar($C_1$-$C_6$) alkyl, $C_1$-$C_{20}$ alkoxy, $C_1$-$C_{20}$ haloalkyl, $C_1$-$C_{20}$ alkoxy alkyl, $C_1$-$C_{20}$ alkanoyloxyalkyl, $C_3$-$C_8$ cycloalkyl, $C_3$-$C_8$ cycloalkyl ($C_1$-$C_6$) alkyl, $C_1$-$C_{20}$ carboxyalkyl or aryl substituted by halogen $C_1$-$C_8$ alkyl, O($C_1$-$C_4$) alkyl, O($C_1$-$C_8$) acyl, nitro, carboxyl or carboethoxy; and X represents a halogen atom or other equivalent organic or inorganic monovalent anion.

The pyridine derivatives of the present invention represented by the formula (I) have cholinesterase inhibitory activity and blood cholesterol lowering activity and are as effective as acetylcholine in the treatment, management, mitigation of conditions or diseases such as hyperlipemia, atherosclerosis, severe myasthenia, Alzheimer's disease, and senile dementia.

Exemplary of the groups represented by $R^1$, $R^2$, (CH)—$R^3$, $R^4$ and $X^-$ in the formula (I) are as follows.

Examples of the "alkyl" groups are straight or branched-chain alkyl groups having 1 to 20 carbon atoms such as methyl, ethyl, propyl, isopropyl, butyl, tert-butyl, pentyl, hexyl, heptyl, octyl, nonyl, decyl, undecyl, etc.

Representative of the "heterocyclic rings" include piperidine, N-($C_1$-$C_6$) alkyl piperidine, N-acylpiperidine, pyrrolidone, morpholine, pyridine, pyrimidine, pyrrole, oxazole and the like.

Examples of the "cycloalkyl" groups having 3 to 8 carbon atoms are cyclopropyl, cyclobutyl, cyclopentyl, cyclohexyl, cycloheptyl, cyclooctyl, etc.

Examples of the "cycloalkyl-lower alkyl" groups having 3 to 8 carbon atoms in the cycloalkyl moiety are those having 1 to 6 carbon atoms in the alkyl moiety including cyclopropylmethyl, 2-cyclopropylethyl, 3-cyclopropylpropyl, 4-cyclopropylbutyl, 6-cyclopropylhexyl, cyclobutylmethyl, 2-cyclobutylethyl, 4-cyclobutylbutyl, 6-cyclobutylhexyl, cyclopentylmethyl, 2-cyclopentylethyl, 4-cyclopentylbutyl, cyclohexylmethyl, 2-cyclohexylethyl, 1-cyclohexylethyl, 3-cyclohexylpropyl, 4-cyclohexylbutyl, 1,1-dimethyl-2-cyclohexylethyl, 5-cyclohexylpentyl, 6-cyclohexylhexyl, 2-methyl-3-cyclohexylpropyl, cycloheptylmethyl, 2-cycloheptylethyl, 1-cycloheptylethyl, cyclooctylmethyl, 2-cyclooctylethyl, 4-cyclooctylbutyl, 6-cyclooctylhexyl, etc.

Examples of "ar($C_1$-$C_6$) alkyl" groups are benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, etc.

Examples of $X^-$ include fluorine, chlorine, bromine, iodine, methanesulfonate, fluorosulfonate, tosylate and the like.

The "acyl" groups include formyl, acetyl, propionyl, benzoyl, etc.

It is further noted that the term "substituted" in reference to the aryl function denotes that same may be substituted with any one or more of the recited substituents.

The present pyridine derivatives of the formula (I) can be prepared by various processes; for example, by the process schematically shown below wherein $R^1$, $R^2$, (CH)—$R^3$, $R^4$ and X are as defined above.

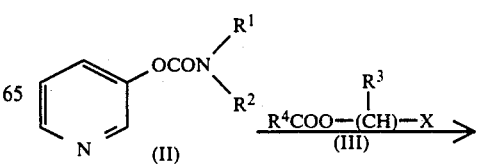

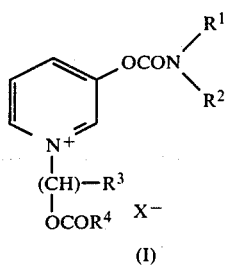

The pyridine derivatives of the formula (II) to be used as starting materials are known as are the alpha-haloester derivatives of the formula (III) which can be easily prepared by the known methods [L. H. Ulich and Roger Adams; *J. Am. Chem. Soc.* 48, 651 (1921) and N. Bodor; *J. Med. Chem.* 23, 469 (1980)].

The reaction of the pyridine derivative with the alphahaloester derivative may generally be carried out in the absence or presence of a suitable solvent, and preferably in the absence of a solvent.

Useful solvents are any of those which do not adversely affect the reaction and which include aromatic hydrocarbons such as benzene, toluene, xylene, etc; aliphatic hydrocarbons such as hexane, heptane and the like; ethers such as diethylether, diisopropyl ether, tetrahydrofuran, ethyleneglycol, dimethyl ether, diethylene dimethyl ether, dioxane and the like, alcohols such as methanol, ethanol, isopropanol, etc.; ketones such as acetone or the like; esters such as ethylacetate; acetonitrile, dimethylformamide, dimethylsulfoxide, hexamethylphosphoric triamide and the like.

Generally, the reaction can be carried out at about 30° C. to about 120° C., preferably about 60° C. to about 100° C., and is completed in from about 10 minutes up to about 12 hours.

There is not any specific limitation as to the relative amounts of alpha-haloester derivative (III) and the pyridine derivative (II) to be used in the above reaction, and, accordingly, the amounts can be selected from a wide range. Generally, the latter is used in an equimolar to an excess amount, preferably an amount of about 1 to about 2 moles per mole of the former.

The compounds thus obtained can be readily isolated and purified by conventional separation means such as solvent extraction, dilution or recrystallization methods, column chromatography, preparative thin-layer chromatography and the like.

The pyridine derivatives of the present invention include not only those of the formula (I) but also the optical isomers thereof and pharmaceutically acceptable non-toxic salts thereof.

The present invention is also directed to pharmaceutical compositions comprising the pyridine derivatives of formula (I) as cholinesterase inhibitors in admixture with conventional pharmaceutical carriers. Examples of useful carriers are those usually used for preparing pharmaceutical compositions in the desired form such as diluents or excipients, including fillers, extenders, binders, wetting agents, disintegrators, surfactants, lubricants, etc. The pharmaceutical compositions can be in any one of various dosage forms including tablets, pills, powder, solutions, suspensions, emulsions, granules, capsules, suppositories, injections (solutions and suspensions), etc. Examples of useful carriers for preparing tablets include a wide variety of those known in the pharmaceutical formulation art; for example, excipients such as lactose, sucrose, sodium chloride, glucose, urea, starch, calcium carbonate, kaolin, crystalline cellulose, silicic acid and the like; binding agents such as water, ethanol, propanol, simple syrup, glucose solution, starch solution, gelatin solution, carboxymethylcellulose, shellac, methylcellulose, calcium phosphate, polyvinylpyrrolidone and the like; disintegrators such as dried starch, sodium alginate, agar-agar powder, laminalia powder, sodium hydrogencarbonate, calcium carbonate, polyoxyethylene sorbitan fatty acid ester, sodium laurylsulfate, monoglyceride of stearic acid, starch, lactose and the like; disintegration inhibitors such as sucrose, stearin, coconut butter, hydrogenated oil, etc.; adsorption accelerators such as quaternary ammonium base, sodium laurylsulfate and the like; wetting agents such as glycerin, starch and the like; adsorbing agents such as starch, lactose, kaolin, bentonite, colloidal silicic acid and the like; and lubricants such as purified talc, stearic acid salt, boric acid powder, polyethylene glycol etc. When desired, tablets in accordance with the present invention may be provided with a typical coating. Useful coatings are sugar-coated, gelatin-coated, enteric coated, film-coated, double-layer and multiple-layer tablets. Suppositories may be formulated with the use of a wide variety of known carriers, such as polyethylene glycol, cacao fat, higher alcohols, esters of higher alcohols, gelatin, and semi-synthetic glycerides. The solutions, emulsions and suspensions for injection should be sterilized and are preferably rendered isotonic with the blood by the addition of suitable buffers. For the preparation of such solutions, emulsions and suspensions, any inert diluent may be utilized such as water, ethyl alcohol, propylene glycol, ethoxylated isostearyl alcohol, polyoxyisostearyl alcohol, polyoxyethylene sorbitol, sorbitan esters and the like. For the preparation of solutions, sodium chloride, glucose or glycerin may be incorporated therein in an amount sufficient to render the solutions isotonic. Such solutions may further incorporate usual solubilizing agents, other buffers, analgesics, preservatives, etc. The present compositions may contain coloring agents, preservatives, perfumes, flavoring agents, sweetening agents, etc. as well as other active drugs including combinations of one or more of the pyridine derivatives of the present invention.

The amount of the anticholinesterase compound of formula (I) to be contained in the cholinesterase inhibitor formulations of the present invention is not specifically limited, but usually the amount will be about 1 to about 70% by weight of the whole composition.

The cholinesterase inhibitors of the present invention are not specifically limited to any particular mode of administration and can be given by any suitable method in accordance with the particular form of the composition. For example, tablets, pills, solutions, suspensions, emulsions, granules and capsules are administered orally. Injections are given intravenously, singly or as admixed with an auxiliary solution of glucose, amino acids, etc. When desired, injections are administered intramuscularly, intradermally, subcutaneously or intraperitoneally.

The cholinesterase inhibitors of the present invention are administered in an anticholinesterase or antihypercholesterolemic therapeutically effective amount suitably determined with respect to the age, weight and condition of the patient and the nature and severity of the disease state. Usually the compositions are administered in a daily dose of about 4 micrograms to about 2 milligrams per kg of body weight, calculated as the compound (I) or a salt thereof, for human patients. The composition is given in three to four divided doses daily.

Certain of the preferred compounds in accordance with the present invention were subjected to pharmacological testing according to the following procedures.

Test Compounds

| Compound No. | Name of the compound |
|---|---|
| 1 | 3-(Dimethylcarbamoyloxy)-1-(pivalyloxymethyl)pyridinium chloride |
| 2 | 3-(Dimethylcarbamoyloxy)-1-(phenylcarbonyloxymethyl)pyridinium chloride |

Pharmacological Test (a) Effects of the Cholinesterase Inhibitors on the Plasma Lipid in the Hypercholesterolemic Rats Male Wistar rats, in 4 groups each consisting of 5 rats, 7 weeks old, were used. For one week before drug administration they were fed rat chow containing 1% cholesterol and 0.5% cholic acid.

On the day of the experiment, the test compounds were intraperitoneally administered three times at two-hour intervals (the test compounds 1 and 2, 2 mg/kg×3, neostigmine bromide, 0.2 mg/kg×3, saline, 2 ml/kg×3). Six hours after the first administration, the animals were sacrificed and all blood collected from the abdominal vena cava. A Wako kit using the o-phthaldehyde method was used for the measurement of total cholesterol, and a Wako kit using the heparin/calcium precipitation method for the measurement of LDL cholesterol.

Table 1 below shows the results.

TABLE 1

|  | Total cholesterol (mg %) | LDL-cholesterol (mg %) |
|---|---|---|
| Saline | 125.2 ± 9.3 | 76.4 ± 12.4 |
| Neostigmine bromide | 131.2 ± 11.8 | 76.6 ± 10.7 |
| Test compound 1 | 77.6 ± 6.7* | 49.1 ± 12.6 |
| Test compound 2 | 146.1 ± 27.0 | 56.3 ± 15.9 |

Values indicate mean S.E. ± (n = 5)
*p < 0.01 significant difference (b) Test for Inhibition of Cholinesterase Activity An in vitro test using a Sigma cholinesterase standard and a Wako kit was carried out on the test compounds 1, 2 as well as neostigmine bromide.

To 4.9 ml of a substrate buffer solution (acetylcholine and m-nitrophenol), 0.1 ml of the test solution ($10^{-8}$–$10^{-4}$ mol) was added. After preincubation at 37° C. for 3 min., reaction was started by the addition of 0.05 ml of an enzyme solution (15.15 U/ml) to the mixture followed by an incubation at 37° C. for 60 min. Then the reaction was stopped by the addition of two drops of neostigmine solution, and the absorbance was determined at 420 nm.

FIG. 1 shows the result. In FIG. 1, the mark ● indicates neostigmine bromide; the mark Δ, test compound 1; and the mark ○, test compound 2. FIG. 1 is a graph showing the relationship between the concentration of the test compounds and inhibition (%) of cholinesterase activity.

(c) Acute Toxicity Test

Each of the test compounds 1a and 2 was interaperitoneally administered to 5 male Wistar rats at the dosage of 6 mg/kg, and neostigmine bromide was administered at the dosage of 0.5 mg/kg.

All the rats appeared normal after administration of the test compounds 1 and 2. But all the rats were dead after administration of neostigmine bromide. Based on the foregoing results, it is estimated that the compounds of the present invention possess at least 12 times lower toxicity than neostigmine bromide.

The present invention will be described below in more detail with reference to certain preferred embodiments thereof in the following non-limiting examples illustrating the preparation of the present compounds.

EXAMPLE 1

3-Dimethylcarbamoyloxypyridine (1.66 g) and chloromethyl acetate (2.18 g) were stirred at 90° C. for 1 hr. The hot reaction mixture was poured into 100 ml of anhydrous diethylether with vigorous stirring. The supernatant was removed by decantation followed by addition of 500 ml of diethylether. Again, the supernatant was removed by decantation. These procedures were repeated three times. The solvent was removed under reduced pressure to give 2.56 g of 1-(acetyloxymethyl)-3-(dimethylcarbamoyloxy)pyridinium chloride as oil. The structure was determined by N.M.R.

Elemental analysis for $C_{11}H_{15}N_2O_4Cl$:

|  | C | H | N |
|---|---|---|---|
| Calcd. (%) | 48.10 | 5.50 | 10.20 |
| Found (%) | 47.83 | 5.72 | 9.98 |

N.M.R. (CDCl$_3$, ppm): δ 9.50 (2H, m), 8.50 (2H, m), 6.80 (2H, s), 3.10 (3H, s), 3.00 (3H, s), 2.10 (3H, s).

EXAMPLE 2

3-Dimethylcarbamoyloxypyridine (1.66 g) and chloromethylpropionate (2.46 g) were heated to 90° C. with stirring for 2 hrs. The reaction mixture was treated in a similar manner as described in Example 1 to give 2.75 g of 3-(dimethylcarbamoyloxy)-1-(n-propionyloxymethyl)pyridinium chloride as oil. The structure was determined by N.M.R.

Elemental analysis for $C_{12}H_{17}N_2O_4Cl$:

|  | C | H | N |
|---|---|---|---|
| Calcd. (%) | 49.92 | 5.93 | 9.70 |
| Found (%) | 49.66 | 6.01 | 9.35 |

N.M.R. (CDCl$_3$, ppm): δ 9.40 (2H, m), 8.40 (2H, m), 6.85 (2H, s), 3.10 (3H, s), 3.00 (3H, s), 2.40 (2H, q), 1.10 (3H, t).

EXAMPLE 3

3-Dimethylcarbamoyloxypyridine (1.66 g) and chloromethylphenylacetate (2.78 g) were heated to 90° C. with stirring for 3 hrs. The reaction mixture was treated in a similar manner as described in Example 1 to give 3.16 g of 3-(dimethylcarbamoyloxy)-1-(phenylacetyloxymethyl)pyridinium chloride as oil. The structure was determined by N.M.R.

Elemental analysis for $C_{17}H_{19}N_2O_4Cl$:

|            | C     | H    | N    |
|------------|-------|------|------|
| Calcd. (%) | 58.21 | 5.46 | 7.99 |
| Found (%)  | 58.00 | 5.59 | 7.77 |

N.M.R. (CDCl₃, ppm): δ 9.00 (2H, m), 8.40 (2H, m), 7.40 (5H, s), 6.80 (2H, s), 3.70 (2H, s), 3.10 (3H, s), 3.00 (3H, s).

EXAMPLE 4

3-Dimethylcarbamoyloxypyridine (1.66 g) and chloromethylcyclopropanecarboxylate (2.70 g) were heated to 90° C. with stirring for 3 hrs. The reaction mixture was treated in a similar manner as described in Example 1 to give 2.77 g of 3-(dimethylcarbamoyloxy)-1-(cyclopropylcarbonyloxymethyl)pyridinium chloride as oil. The structure was determined by N.M.R.

Elemental analysis for $C_{13}H_{17}N_2O_4Cl$:

|            | C     | H    | N    |
|------------|-------|------|------|
| Calcd. (%) | 51.92 | 5.70 | 9.31 |
| Found (%)  | 51.66 | 5.81 | 9.20 |

N.M.R. (CDCl₃, ppm): δ 9.30 (2H, m), 8.40 (2H, m), 6.85 (2H, s), 3.05 (3H, s), 3.00 (3H, s), 2.0-1.0 (5H, m).

EXAMPLE 5

3-Dimethylcarbamoyloxypyridine (1.66 g) and chloromethylhexanoate (2.0 g) were heated to 90° C. with stirring for 3 hours. The reaction mixture was treated in a similar manner as described in Example 1 to give 2.65 g of 3-(dimethylcarbamoyloxy)-1-(hexanoyloxymethyl)-pyridinium chloride as colorless powdery crystals. It was impossible to precisely measure the melting point because of high hygroscopicity. The structure was determined by N.M.R.

Elemental analysis for $C_{15}H_{23}N_2O_4Cl \cdot H_2O$:

|            | C     | H    | N    |
|------------|-------|------|------|
| Calcd. (%) | 51.65 | 6.64 | 8.03 |
| Found (%)  | 51.33 | 6.94 | 7.93 |

N.M.R. (CDCl₃, ppm): δ 9.40 (2H, m), 8.40 (2H, m), 6.85 (2H, s), 3.10 (3H, s), 3.00 (3H, s), 2.40 (2H, t), 1.80-1.0 (9H, m).

EXAMPLE 6

3-Dimethylcarbamoyloxypyridine (1.66 g) and chloromethylpivalate (2.26 g) were heated to 90° C. with stirring for 2 hrs. The reaction mixture was cooled to room temperature. To this solution was added anhydrous diethylether to crystallize. The crystals were filtered off, washed three times with anhydrous diethyl ether (50 ml×3) and dried under reduced pressure. Recrystallization from acetone-ether (1:2) gave 2.76 g of 3-(dimethylcarbamoyloxy)-1-(pivalyloxymethyl)-pyridinium chloride as colorless powdery crystals, m.p. 154°-155° C.

Elemental analysis for $C_{14}H_{21}N_2O_4Cl$:

|            | C     | H    | N    |
|------------|-------|------|------|
| Calcd. (%) | 53.08 | 6.63 | 8.85 |
| Found (%)  | 53.21 | 6.80 | 8.85 |

N.M.R. (CDCl₃, ppm): δ 9.45 (2H, m), 8.40 (2H, m), 6.90 (2H, s), 3.10 (3H, s), 3.00 (3H, s), 1.10 (9H, s).

EXAMPLE 7

3-Dimethylcarbamoyloxypyridine (4.98 g) and chloromethylbenzoate (5.13 g) were heated to 70° C. with stirring for 4 hrs. The hot reaction mixture was poured into 100 ml of diethyl ether with vigorous stirring. The precipitated solids were filtered off and washed twice with anhydrous diethyl ether (100 ml×2). Recrystallization from acetone gave 8.6 g of 3-(dimethylcarbamoyloxy)-1-(phenylcarbonyloxymethyl)pyridinium chloride as prisms, m.p. 175°-176° C.

Elemental analysis for $C_{16}H_{17}N_2O_4Cl$:

|            | C     | H    | N    |
|------------|-------|------|------|
| Calcd. (%) | 57.06 | 5.05 | 8.32 |
| Found (%)  | 56.97 | 5.12 | 8.27 |

N.M.R. (CDCl₃, ppm): δ 9.67 (2H, m), 8.50 (2H, m), 8.00 (2H, d-d), 7.60-7.35 (3H, m) 7.10 (2H, s), 3.15 (3H, s), 3.00 (3H, s).

EXAMPLES 8 TO 10

Compounds of Examples 8 to 10 as shown below in Table 2 were prepared in the same manner as in Example 6 or 7 by using suitable starting materials.

TABLE 2

$$\underset{\underset{OCOR^4}{|}}{\underset{(CH)-R^3}{\underset{|}{N^+}}} \text{pyridine-OCON} \begin{matrix} R^1 \\ R^2 \end{matrix} \quad X^-$$

| Example | R¹  | R²  | R³ | R⁴                  | X  | Melting point (°C.) |
|---------|-----|-----|----|---------------------|----|---------------------|
| 8       | CH₃ | CH₃ | H  | —CH₂—(cyclobutyl)   | Cl | 106–108             |
| 9       | CH₃ | CH₃ | H  | —(phenyl)           | Cl | 116–117             |
| 10      | CH₃ | CH₃ | H  | —CH₂(CH₂)₉CH₃       | Cl | 85–87               |

Using suitable starting materials and reaction conditions and employing reaction procedures analogous to those of Examples 1–7, the following pyridine derivatives are prepared in like manner as set forth in Table 3 wherein R¹, R², R³, R⁴ and X are as defined before.

TABLE 3

| Example | R¹ | R² | R³ | R⁴ | X |
|---|---|---|---|---|---|
| 11 | —CH$_2$CH$_3$ | —CH$_2$CH$_3$ | —CH$_2$(CH$_3$)$_3$CH$_3$ |  phenyl | Cl |
| 12 | —H | —CH$_2$(CH$_2$)$_5$CH$_3$ | —CH$_2$(CH$_2$)$_2$CH$_2$Cl | —CH$_2$—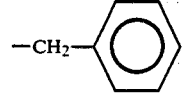 | Cl |
| 13 | —CH$_2$(CH$_2$)$_2$CH$_3$ | —H | —OCH$_2$CH$_3$ | —CH$_2$(CH$_2$)$_2$—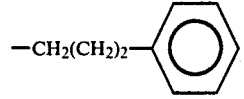 | F |
| 14 | 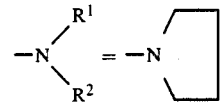 —N(R¹)(R²) = —N(pyrrolidine) | | —CH$_2$CH$_2$Cl | 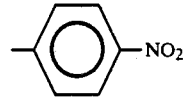 —C$_6$H$_4$—NO$_2$ | Cl |
| 15 | 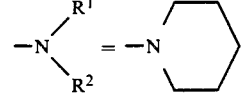 —N(R¹)(R²) = —N(piperidine) | | CH$_3$ | 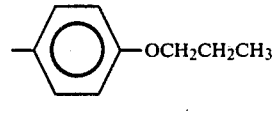 —C$_6$H$_4$—OCH$_2$CH$_3$ | Cl |
| 16 | 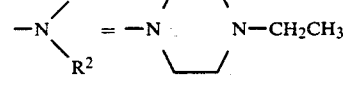 —N(R¹)(R²) = —N(N-ethylpiperazine) | | CH$_3$ | —CH$_2$(CH$_2$)$_6$CH$_3$ | Cl |
| 17 | 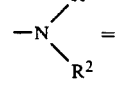 —N(R¹)(R²) = —N(4-(5-chloropentyl)piperazine) | | —CH(CH$_3$)—CH$_2$CH$_3$ | 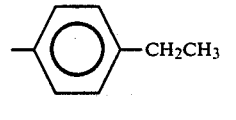 —C$_6$H$_4$—CH$_2$CH$_3$ | Cl |
| 18 | 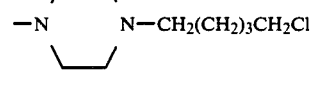 —N(R¹)(R²) = —N(morpholine) | | —CH$_2$—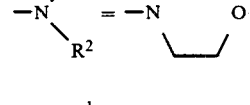 | —CH$_2$CH$_3$ | Br |
| 19 | 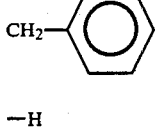 —N(R¹)(R²) = —N(pyrrole) | | —H | —CH$_2$(CH$_2$)$_2$CH$_3$ | Cl |
| 20 | 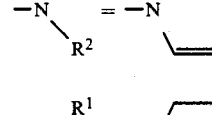 —N(R¹)(R²) = —N(4-ethylpyridine) | | —OCH$_2$CH$_3$ |  phenyl | Cl |
| 21 |  —N(R¹)(R²) = —N(4-(2-butoxyethyl)piperazine) | | —CH$_3$ | 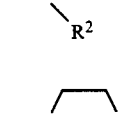 —C$_6$H$_4$—OC(O)CH$_2$CH$_3$ | Cl |

TABLE 3-continued

| Example | R¹ | R² | R³ | R⁴ | X |
|---|---|---|---|---|---|
| 22 | \-N(R¹)(R²) = N-piperazine-N-cyclopropyl | | phenyl | —CH$_2$CH$_3$ | Cl |
| 23 | \-N(R¹)(R²) = N-piperazine-N-(4-ethylphenyl) | | CH$_2$(CH$_2$)$_2$CH$_3$ | —CH$_3$ | Cl |
| 24 | \-N(R¹)(R²) = N-piperazine-N-CH$_2$CH$_2$OC(=O)—CH$_2$CH$_3$ | | —CH$_2$-phenyl | —CH$_2$CH$_3$ | Cl |
| 25 | \-N(R¹)(R²) = N-piperazine-N-(4-chlorophenyl) | | —CH$_2$(CH$_2$)$_2$CH$_3$ | phenyl | Br |
| 26 | \-N(R¹)(R²) = N-pyrrolidine-CH$_2$CH$_3$ | | —H | 2-hydroxycarbonylphenyl (C(=O)OH) | Cl |
| 27 | —CH$_2$CH$_3$ | —CH$_2$CH$_3$ | 4-chlorophenyl | —CH$_2$CH$_2$OC(=O)CH$_3$ | Br |
| 28 | CH$_3$ | —(CH$_2$)$_7$CH$_3$ | —CH$_2$CH$_3$ | —CH$_2$CH$_2$Cl | Cl |
| 29 | —CH$_2$CH$_3$ | —H | —OCH$_2$(CH$_2$)$_2$CH$_3$ | —CH$_2$CH$_2$-cyclopentyl | Cl |
| 30 | \-N(R¹)(R²) = N-morpholine | | —CH$_2$CH$_2$Cl | —CH$_2$(CH$_2$)$_2$CH$_2$COOH | Cl |

Given below are preparation examples using the present compounds.

Tablets having the following formulations were prepared in the conventional manner.

Preparation (Example A)

| | |
|---|---|
| 3-(Dimethylcarbamoyloxy)-1-(pivalyloxymethyl)pyridinum chloride | 5 mg |
| Starch | 132 mg |
| Magnesium stearate | 45 mg |
| Total | 200 mg |

Preparation (Example B)

| | |
|---|---|
| 3-(Dimethylcarbamoyloxy)-1-(phenyl-carbonyloxymethyl)pyridinum chloride | 500 mg |

| -continued | |
|---|---|
| Polyethylene glycol (molecular weight: 4000) | 0.3 g |
| Sodium chloride | 0.9 g |
| Polyoxyethylene sorbitan monooleate | 0.4 g |
| Sodium metabisulfite | 0.1 g |
| Methyl p-hydroxybenzoate | 0.18 g |
| Propyl p-hydroxybenzoate | 0.02 g |
| Distilled water for injection | 100 ml |

The methyl p-hydroxybenzoate, propyl p-hydroxybenzoate, sodium metabisulfite and sodium chloride components were dissolved in distilled water at 80° C. under stirring. The solution obtained was cooled to 40° C., then the compound of the present invention, polyethylene glycol and polyoxyethylene sorbitan monooleate were dissolved in this order in the solution. To this solution was added a sufficient amount of distilled water for injection so as to adjust the final regulated volume, and the mixture was sterilized by sterile filtration by using a suitable filter paper. One milliliter of the resultant solution was introduced into separate ampoules to make injectables.

While the invention has been described and illustrated with reference to certain preferred embodiments thereof, those skilled in the art will appreciate that various changes, modifications and substitutions can be made therein without departing from the spirit of the invention. For example, effective dosages other than the preferred ranges set forth hereinabove may be applicable as a consequence of variations in the responsiveness of the mammal treated, severity of the condition treated, dosage related adverse effects, if any, observed and analogous considerations. Likewise, the specific pharmacological responses observed may vary depending upon the particular relative amounts of active components employed or whether same are used in combination with suitable pharmaceutical carriers, as well as the type of formulation and mode of administration employed, and such expected variations or differences in results are contemplated in accordance with the objects and practices of the present invention. It is intended, therefore, that the invention be limited only by the scope of the claims which follow.

What is claimed is:

1. A pyridine compound of the formula (I) and nontoxic pharmaceutically acceptable salts thereof:

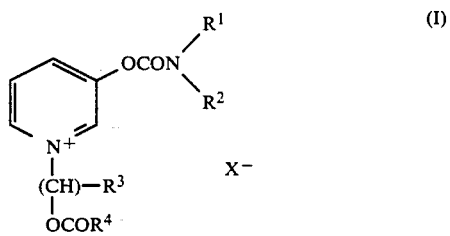

wherein $R^1$ and $R^2$ are the same or different and represent hydrogen or $C_1$-$C_8$ alkyl;

$R^3$ represents hydrogen, $C_1$-$C_{20}$ alkyl, $C_6$-$C_{10}$ aryl, ar($C_1$-$C_6$) alkyl, $C_1$-$C_{20}$ alkoxy, $C_1$-$C_{20}$ haloalkyl, $C_1$-$C_{20}$ alkoxy alkyl, $C_1$-$C_{20}$ alkanoyloxyalkyl, $C_3$-$C_8$ cycloalkyl, $C_3$-$C_8$ cycloalkyl ($C_1$-$C_6$) alkyl or aryl substituted by halogen, $C_1$-$C_8$ alkyl, O($C_1$-$C_4$) alkyl or nitro;

$R^4$ represents hydrogen, $C_1$-$C_{20}$ alkyl, $C_6$-$C_{10}$ aryl, ar($C_1$-$C_6$) alkyl, $C_1$-$C_{20}$ alkoxy, $C_1$-$C_{20}$ haloalkyl, $C_1$-$C_{20}$ alkoxy alkyl, $C_1$-$C_{20}$ alkanoyloxyalkyl, $C_3$-$C_8$ cycloalkyl, $C_3$-$C_8$ cycloalkyl ($C_1$-$C_6$) alkyl, $C_1$-$C_{20}$ carboxyalkyl or aryl substituted by halogen, $C_1$-$C_8$ alkyl, O($C_1$-$C_4$) alkyl, $C_1$-$C_8$ alkanoyloxy, nitro or carboxyl; and X represents a halogen atom or other equivalent organic or inorganic monovalent anion.

2. A pyridine compound as defined in claim 1 wherein $R^1$ and $R^2$ are the same or different and represent hydrogen or $C_1$-$C_8$ alkyl; $R^3$ is $C_1$-$C_8$ alkyl; $R^4$ is $C_1$-$C_{20}$ alkyl, $C_3$-$C_8$ cycloalkyl, $C_3$-$C_8$ cycloalkyl ($C_1$-$C_6$) alkyl, phenyl or phenyl ($C_1$-$C_6$) alkyl and X is halogen.

3. A pyridine compound as defined by claim 1 wherein $R^1$ and $R^2$ independently represent hydrogen or methyl.

4. A pyridine compound as defined by claim 1 selected from the group consisting of 3-(dimethylcarbamoyloxy)-1-(pivalyloxymethyl)pyridinium chloride, 3-(dimethylcarbamoyloxy)-1-(phenylcarbonyloxymethyl)pyridinium chloride, 3-(dimethylcarbamoyloxy)-1-(n-propionyloxymethyl)pyridinium chloride, or 3-(dimethylcarbomoyloxy)-1-(phenylacetyloxy methyl)-pyridinium chloride.

5. A pyridine compound as defined by claim 1, wherein X is chloride.

6. An anticholinesterase composition comprising an anticholinesterase effective amount of a compound as defined by claim 1 and a pharmaceutically acceptable carrier.

7. A composition as defined by claim 6, wherein said compound comprises between about 1 to about 70% by weight of the total composition.

8. A method of providing an anticholinesterase effect in mammals in need thereof comprising administering thereto an anticholinesterase effective amount of a compound as defined by claim 1.

9. A method as defined by claim 8, wherein said amount ranges between about 4 µg/kg. to about 2 mg/kg. of body weight per day.

10. An antihypercholesterolemic composition comprising an antihypercholesterolemic effective amount of a compound as defined by claim 1 and a pharmaceutically acceptable carrier.

11. A composition as defined by claim 10, wherein said compound comprises between about 1 to about 70% by weight of the total composition.

12. A method of providing an antihypercholesterolemic effect in mammals in need thereof comprising administering thereto an antihypercholesterolemic effective amount of a compound as defined by claim 1.

13. A method as defined by claim 12, wherein said amount ranges between about 4 µg/kg. to about 2 mg/kg. of body weight per day.

* * * * *